(12) United States Patent
Cooke

(10) Patent No.: US 8,137,287 B2
(45) Date of Patent: Mar. 20, 2012

(54) BIOPSY DEVICE

(75) Inventor: David Cooke, Harvard, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 12/114,308

(22) Filed: May 2, 2008

(65) Prior Publication Data

US 2008/0287825 A1 Nov. 20, 2008

Related U.S. Application Data

(60) Provisional application No. 60/917,759, filed on May 14, 2007.

(51) Int. Cl.
*A61B 10/00* (2006.01)
(52) U.S. Cl. ........................................ 600/562
(58) Field of Classification Search .................. 600/562, 600/564
See application file for complete search history.

(56) References Cited

U.S. PATENT DOCUMENTS

| | | | |
|---|---|---|---|
| 4,274,414 A | 6/1981 | Johnson et al. | |
| 4,844,064 A | 7/1989 | Thimsen et al. | |
| 4,953,558 A | 9/1990 | Akerfeldt | |
| 5,092,870 A | 3/1992 | Mittermeier | |
| 5,195,533 A | 3/1993 | Chin et al. | |
| 5,368,045 A | 11/1994 | Clement et al. | |
| 5,476,101 A | 12/1995 | Schramm et al. | |
| 5,507,298 A | 4/1996 | Schramm et al. | |
| 5,660,186 A | 8/1997 | Bachir | |
| 5,685,852 A | 11/1997 | Turkel et al. | |
| 5,718,237 A | 2/1998 | Haaga | |
| 5,842,999 A | 12/1998 | Pruit et al. | |
| 5,989,196 A | 11/1999 | Chu et al. | |
| 5,993,399 A | 11/1999 | Pruit et al. | |
| 6,015,391 A | 1/2000 | Rishton et al. | |
| 6,033,411 A | 3/2000 | Preissman | |
| 6,050,955 A | 4/2000 | Bryan et al. | |
| 6,086,543 A | 7/2000 | Anderson et al. | |
| 6,126,617 A | 10/2000 | Weilandt et al. | |
| 6,142,955 A | 11/2000 | Farascioni et al. | |
| 6,165,136 A | 12/2000 | Nishtala | |
| 6,221,030 B1 | 4/2001 | Avaltroni et al. | |
| 6,358,217 B1 * | 3/2002 | Bourassa | 600/567 |
| 6,402,701 B1 | 6/2002 | Kaplan et al. | |
| 6,476,101 B2 | 11/2002 | Schramm et al. | |
| 6,488,636 B2 | 12/2002 | Bryan et al. | |
| 6,497,706 B1 | 12/2002 | Burbank et al. | |
| 6,620,111 B2 | 9/2003 | Stephens et al. | |

(Continued)

FOREIGN PATENT DOCUMENTS

EP 0 536 888 4/2003

(Continued)

OTHER PUBLICATIONS

International Preliminary Report on Patentability issued on Nov. 26, 2009 in PCT application: PCT/US2008/062334, filed on May 2, 2008.

*Primary Examiner* — Max Hindenburg
*Assistant Examiner* — Renee Danega
(74) *Attorney, Agent, or Firm* — Fish & Richardson P.C.

(57) ABSTRACT

Medical instruments and methods of using medical instruments are claimed.

10 Claims, 18 Drawing Sheets

U.S. PATENT DOCUMENTS

| | | |
|---|---|---|
| 6,730,045 B2 | 5/2004 | Finer |
| 6,849,080 B2 | 2/2005 | Lee et al. |
| 7,008,382 B2 | 3/2006 | Adams et al. |
| 7,022,085 B2 | 4/2006 | Cooke et al. |
| 7,201,722 B2 | 4/2007 | Krueger |
| 7,449,000 B2 | 11/2008 | Adams et al. |
| 2004/0097832 A1 * | 5/2004 | Adams et al. ............ 600/564 |
| 2005/0124914 A1 | 6/2005 | DiCarlo et al. |
| 2005/0277845 A1 | 12/2005 | Cooke et al. |
| 2006/0195044 A1 | 8/2006 | Cooke et al. |
| 2008/0269638 A1 | 10/2008 | Cooke et al. |
| 2008/0287825 A1 | 11/2008 | Cooke et al. |

FOREIGN PATENT DOCUMENTS

| | | |
|---|---|---|
| JP | 1-198537 | 8/1989 |
| JP | 4-506758 | 11/1992 |
| JP | 6-197898 | 7/1994 |
| JP | 10-179592 | 7/1998 |
| JP | 2000-506044 | 5/2000 |
| JP | 2002-000609 | 1/2002 |
| JP | 2002-514458 | 5/2002 |
| WO | 2004/045415 | 6/2004 |
| WO | 2004/045417 | 6/2004 |
| WO | 2005/055833 | 6/2005 |
| WO | 2005/117683 | 12/2005 |

* cited by examiner

BIOPSY DEVICE

CROSS-REFERENCE TO RELATED APPLICATIONS

This application claims priority under 35 USC §119(e) to U.S. Provisional Patent Application Ser. No. 60/917,759, filed on May 14, 2007, the entire contents of which are hereby incorporated by reference.

TECHNICAL FIELD

This disclosure relates to medical instruments.

BACKGROUND

Biopsy systems can be used to obtain a tissue specimen from a subject.

SUMMARY

In one aspect, a device includes: a housing including a stop; a cannula having a portion in the housing; and a movable cannula block in the housing, the moveable cannula block attached to the cannula, the movable cannula block having a distal end with a face that is asymmetric with respect to the stop. Embodiments of the device can include one or more of the following features.

In some embodiments, the face of the cannula block includes a recessed portion disposed in alignment with a contact portion of the stop. In some cases, the recessed portion is located at one edge of the face.

In some embodiments, the housing includes a wall with a gap sized to accommodate a portion of the cannula block. In some cases, the wall with the gap is a side wall of a track in which the cannula block is disposed.

In some embodiments, the stop is disposed at a distal end of the housing.

In some embodiments, devices also include a stylet disposed coaxially with the cannula, the stylet at least partially within the cannula.

In some embodiments, the housing includes ribs defining a channel that receives at least part of the cannula block, the channel having a channel width. In some cases, the cannula block has a middle portion disposed proximally of the asymmetric distal end of the cannula block and a distal end width is greater than a width of the middle portion and less than the channel width.

In another aspect, a device includes: a housing including a stop; a longitudinally extending first member having a first portion in the housing and a second portion extending out of the housing; and a movable second member in the housing, the second member being connected to the first member, the second member having a distal end with a face that is asymmetric with respect to the stop, the movable second member configured to change movement of the second member from a second direction to a second direction that includes a component transverse to the second direction upon contact with the stop. Embodiments of the device can include one or more of the following features.

In some embodiments, the face of the second member includes a recessed portion disposed in alignment with a contact portion of the stop. In some cases, the recessed portion is located at one edge of the face.

In some embodiments, the housing comprises a wall with a gap sized to accommodate a portion of the movable second member. In some cases, the wall with the gap is a side wall of a track in which the second member is disposed.

In some embodiments, the housing includes ribs defining a channel that receives at least part of the second member, the channel having a channel width. In some cases, the second member has a middle portion disposed proximally of the asymmetric distal end of the second member and a distal end width is greater than a middle portion width and less than the channel width.

In another aspect, a method of operating a medical instrument includes: moving a first member connected to a cannula from a retracted position to an extended position such that an asymmetric end of the first member contacts a stop of the medical instrument off-centered relative to a longitudinal axis of the cannula. Embodiments of the method can include one or more of the following features.

In some embodiments, the method also includes changing the direction of movement of the first member from a substantially linear first direction to a second direction that includes a component transverse to the first direction. In some cases, the method also includes stopping the movement of the first member.

In some embodiments, the method also includes moving a portion of the first member towards a recessed portion of the medical instrument.

Embodiments can include one or more of the following advantages.

In some embodiments, devices and methods as described herein can allow for use of a biopsy device with little or no recoil of the cannula and cannula block. This can, for example, allow for more precise and/or reproducible use of the biopsy device.

In certain embodiments, cannula blocks as described herein can be designed so that they may be used to replace existing cannula blocks (e.g., with faces that are symmetric relative to the stops).

The details of one or more embodiments of the invention are set forth in the accompanying drawings and the description below.

Other features and advantages will be apparent from the description and drawings, and from the claims.

DESCRIPTION OF DRAWINGS

Like reference symbols in the various drawings indicate like elements.

DETAILED DESCRIPTION

Figure 1A:
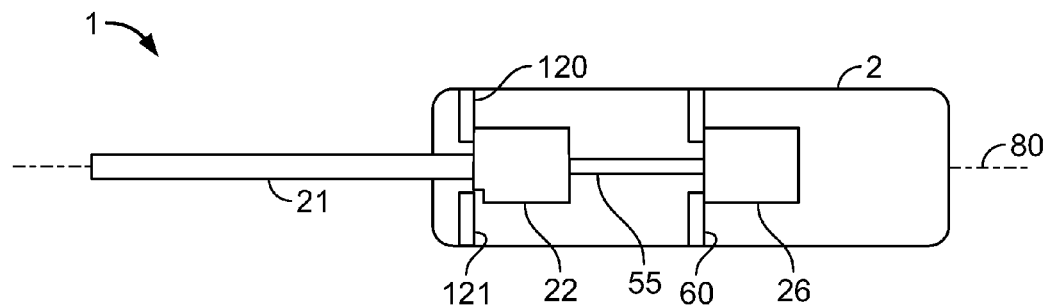
FIGS. 1A-1F are schematic views of an embodiment of a biopsy instrument at various stages of operation.
Figure 1B:
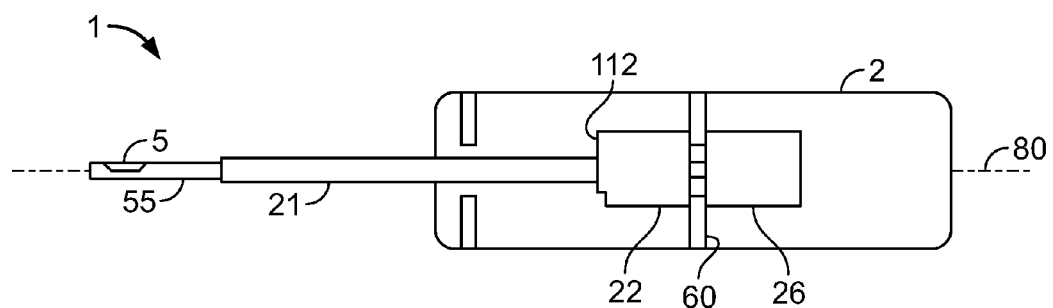
Figure 1C:
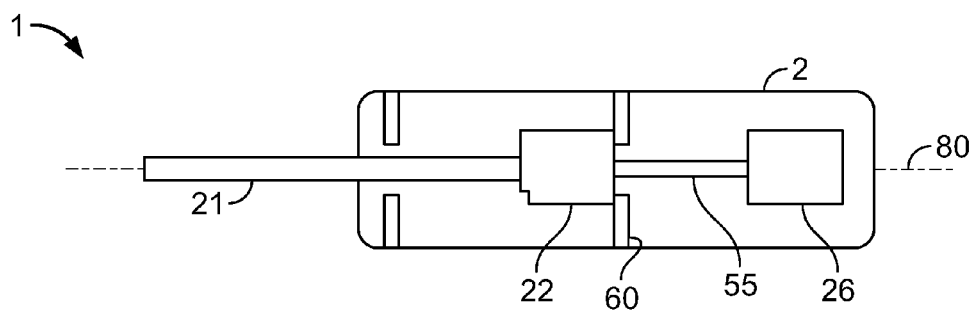
Figure 1D:
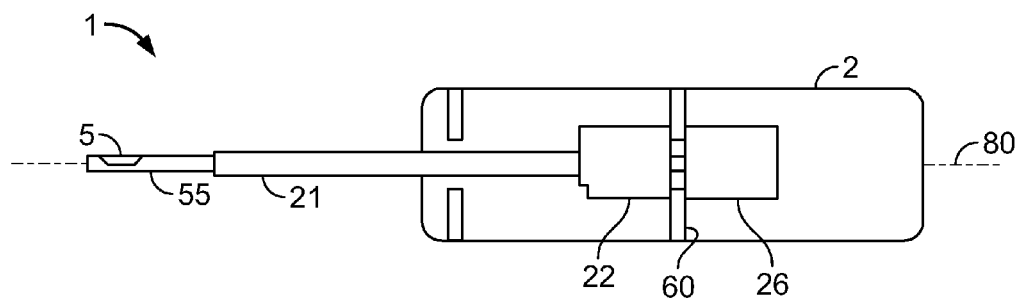

FIGS. 1A-1D schematically illustrate the operation of an embodiment of a biopsy device 1 that includes a cannula 21 disposed coaxially around a stylet 55 (i.e., at rest cannula 21 and stylet 55 share a common axis 80). Stylet 55 and cannula 21 are configured to be axially movable relative to each other, between retracted positions and extended positions. Stylet 55 and cannula 21 are attached to a stylet block 26 and a cannula block 22, respectively, which are mounted inside housing 2. Initially, both stylet 55 and cannula 21 are in their extended positions (see FIG. 1A). An operator prepares biopsy device 1 for use by moving cannula 21 to its retracted position (see FIG. 1B) and then moving stylet 55 to its retracted position (see FIG. 1C). When the operator actuates biopsy device 1, stylet 55 moves rapidly to its extended position. Contact between stylet block 26 and stop block 60 stops the forward movement of stylet block 26 and stylet 55 (see FIG. 1D). As stylet block 26 contacts stop 60, a tissue specimen prolapses into a notch 5 located near the distal end of stylet 55 and cannula block 22 is actuated. While the distal movement of stylet 55 ceases, cannula 21 moves over stylet 55 to the extended position of cannula 21, thereby severing the tissue specimen in notch 5 from the surrounding tissue mass.

Figure 1E:
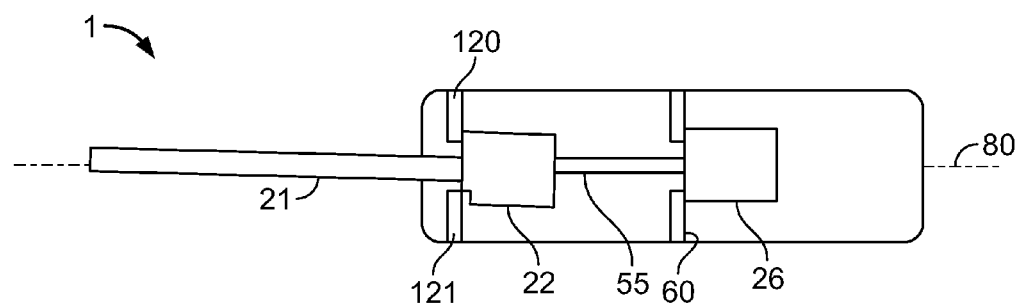
Figure 1F:
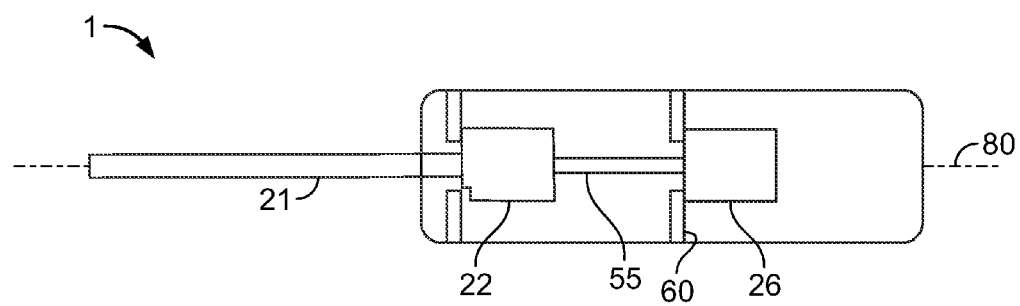

Cannula block 22 has a face 112 that is asymmetric relative to stops 120, 121. As cannula 21 reaches its extended position, cannula block sequentially contacts stop 120, rotates slightly relative to stylet 55, and then contacts stop 121 (see FIG. 1E). Friction between stylet 55 and cannula 21 can decrease or prevent recoil of cannula 21 and cannula block 22. Cannula 21 then rotates back into alignment with axis 80 (see FIG. 1F). The operator can then withdraw biopsy device 1 from the patient and conduct testing on the collected tissue sample.

Figure 2:
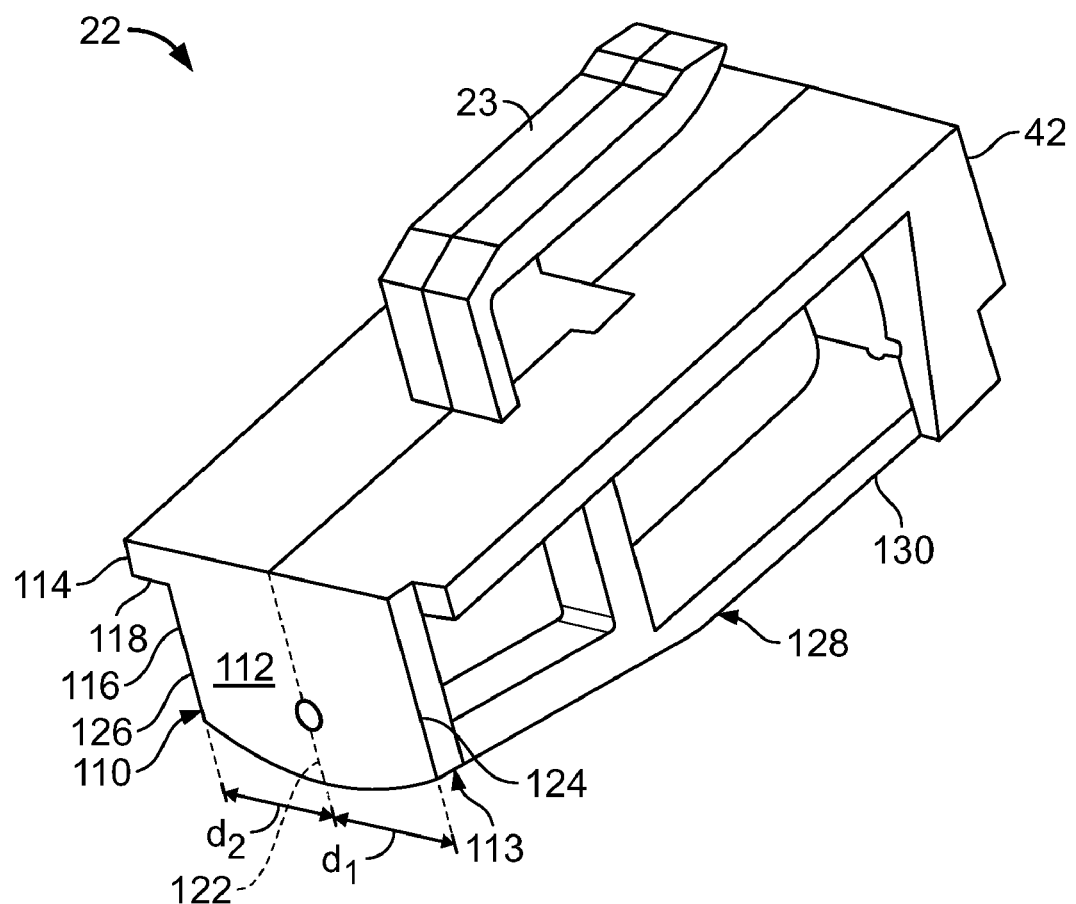
FIG. 2 is a perspective view of an embodiment of a cannula block.

FIG. 2 shows an embodiment of cannula block 22 that has a cannula block body 110 with asymmetric face 112. A distance $d_1$ from a centerline 122 of face 112 to a first lateral edge 124 is less than a distance $d_2$ from centerline 122 to an opposite second lateral edge 126. In effect, a corner of the cannula block 22 has been removed. The asymmetry of face 112 can be achieved by machining a cannula block after it has been formed or by forming a cannula block (e.g., by molding) that includes an asymmetric face 112 from the outset. Other embodiments of cannula blocks can have other configurations of asymmetric faces designed to achieve other degrees of rotation and/or for use with other biopsy devices.

Cannula block body 110 extends axially from face 112 to cannula block retentive portions 42. Cannula block hook 23 extends outwards from a first portion 114 of cannula block body 110. First portion 114 extends laterally outward relative to a second portion 116 of cannula block body 110 thus forming a shoulder 118. Shoulder 118 provides a riding surface which helps position cannula block 22 when cannula block 22 is installed in biopsy instrument 1. Second portion 116 of cannula body 128 defines a relief portion 130 that has a reduced width relative to other parts of second portion 116.

Figure 3A:
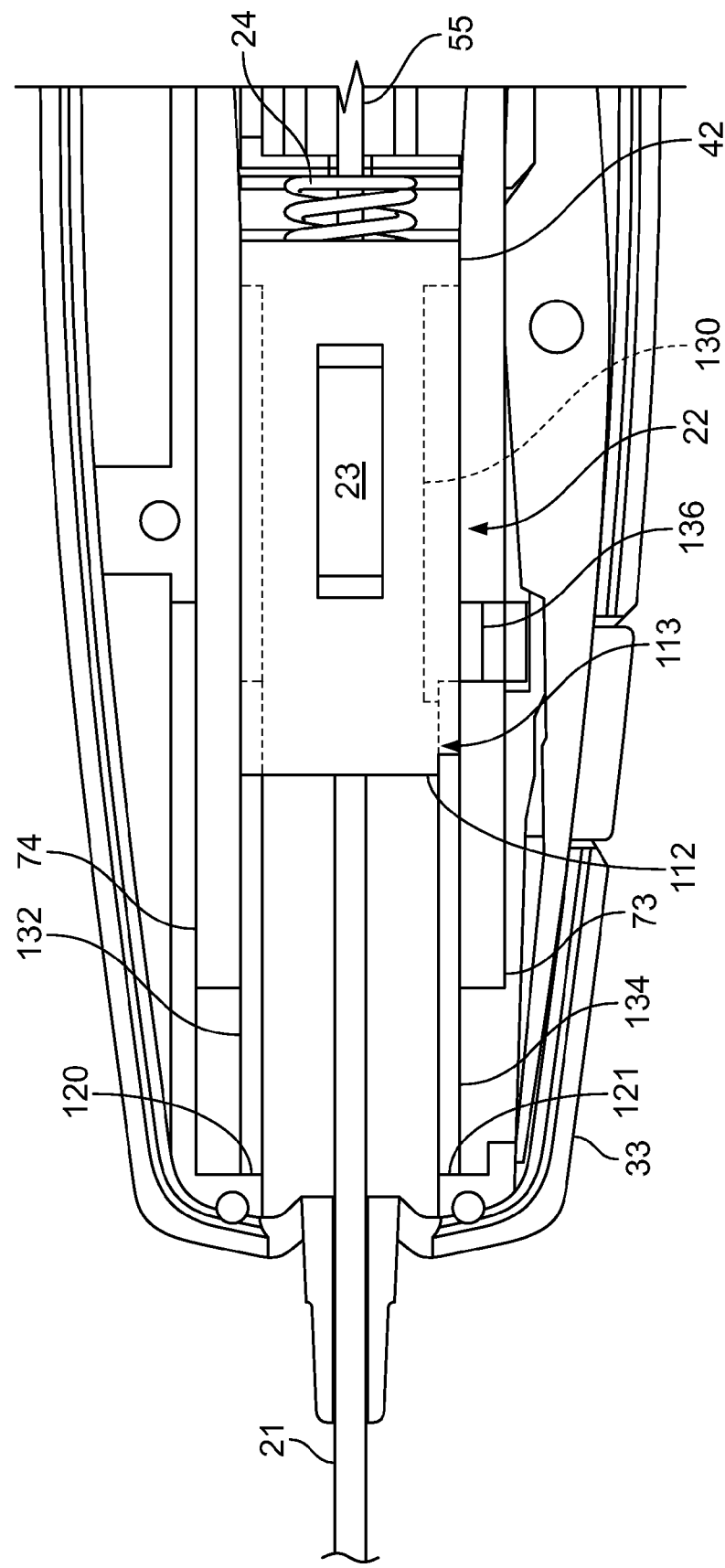
FIGS. 3A-3D illustrate a portion of an embodiment of a biopsy instrument including the cannula block of FIG. 2 at various stages of operation.
Figure 3B:
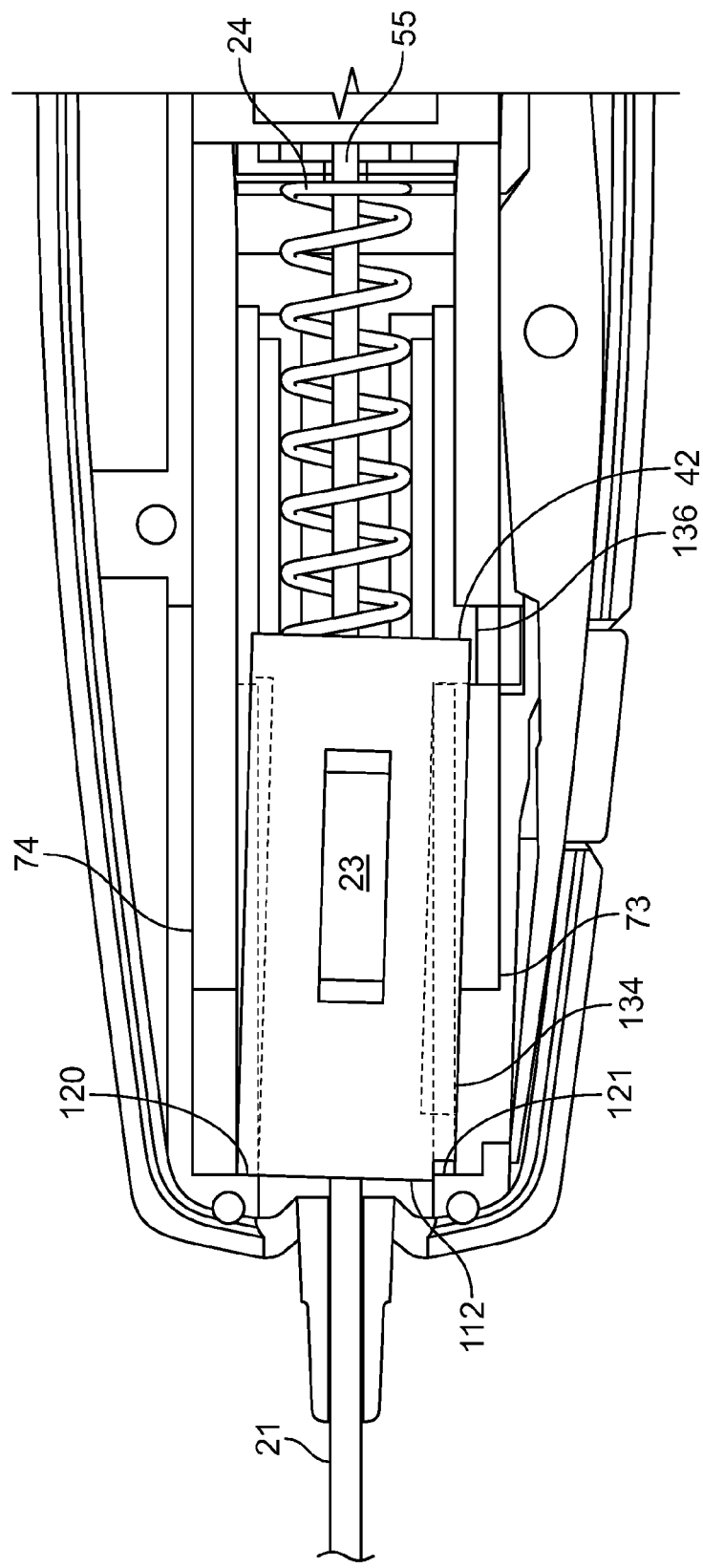
Figure 3C:
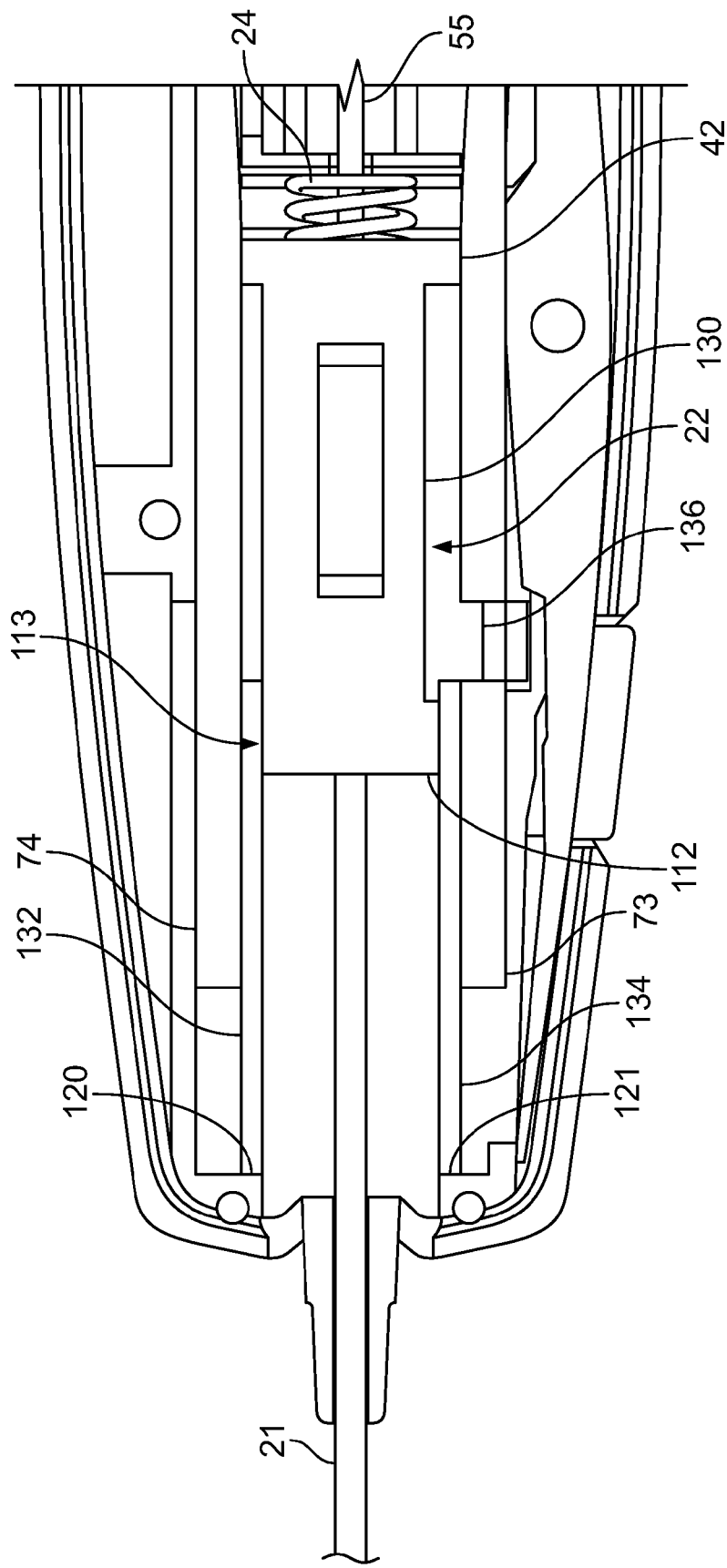
Figure 3D:
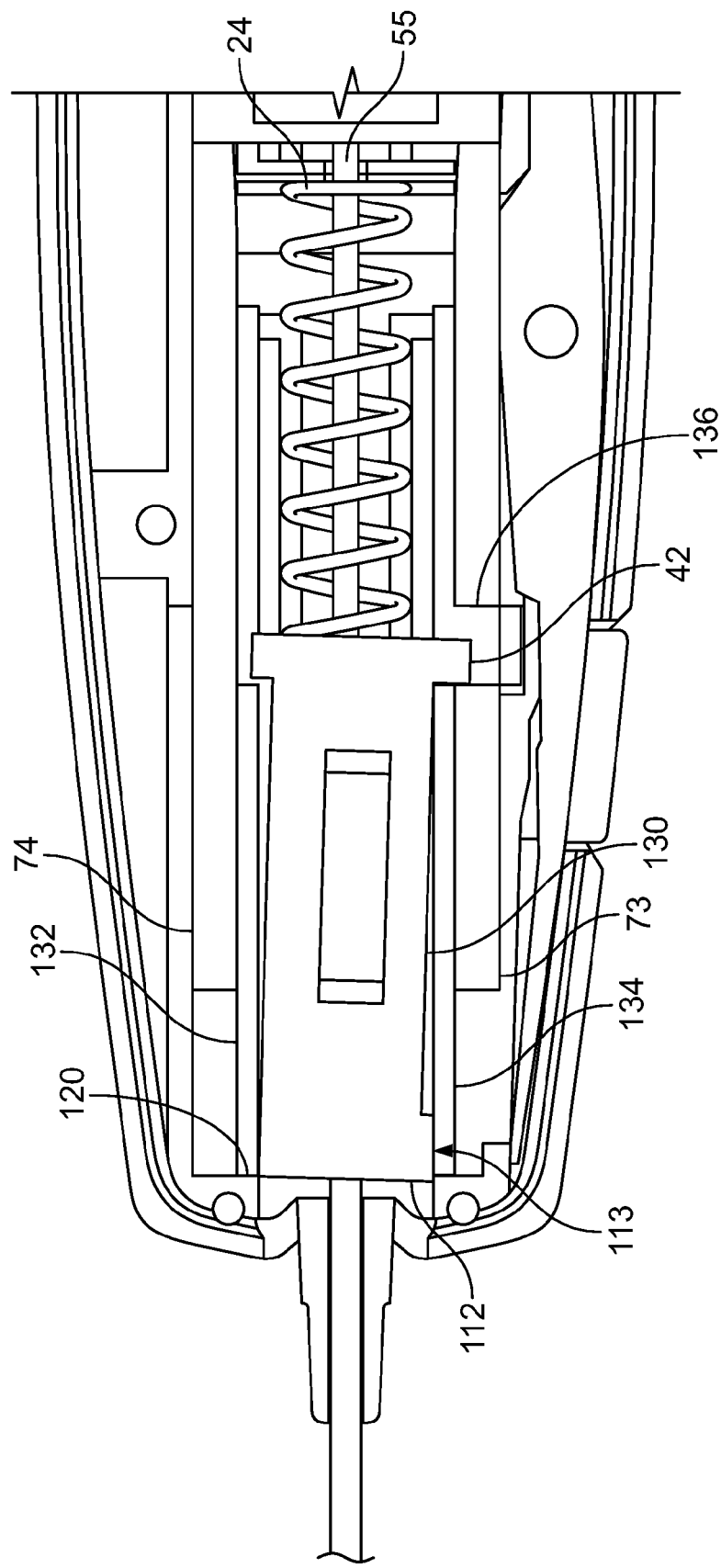
Figure 4:
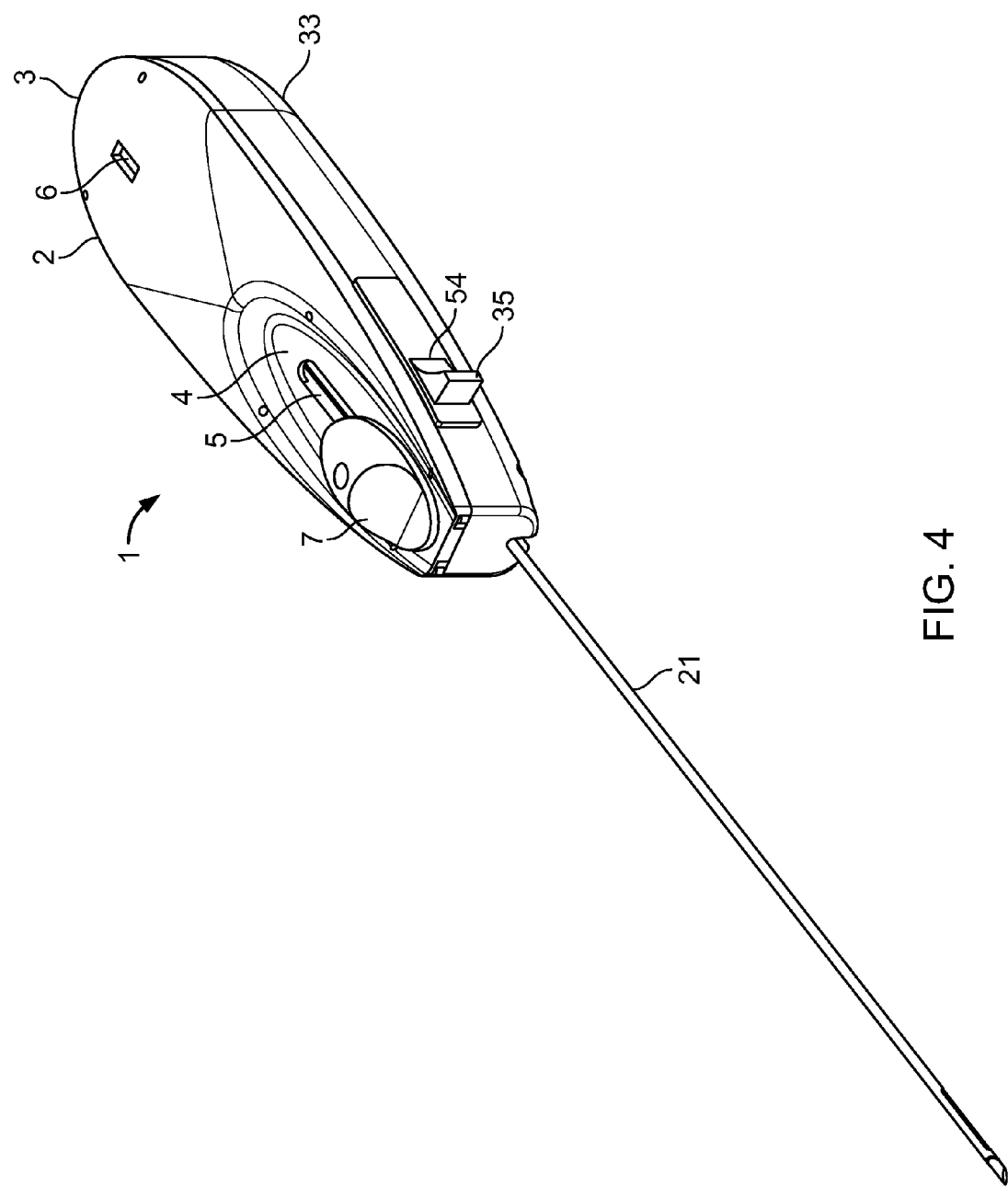
FIG. 4 is a perspective view of an embodiment of a biopsy instrument.

FIGS. 3A-3D illustrate the operation of an embodiment of biopsy device 1 incorporating the embodiment of cannula block 22 shown in FIG. 2. FIGS. 3A and 3B show a portion of biopsy device 1 with cannula block 22 in, respectively, retracted and extended positions with dashed lines indicating the position of components underlying first portion 114 of cannula block body 110. FIGS. 3C and 3D show a portion of biopsy device 1 with a partial cut away view of cannula block 22 (i.e., without first portion 114 of cannula block body 110) in, respectively, retracted and extended positions.

Cannula block 22 is placed in bottom shell 33 of housing 2 between walls 73, 74 of bottom shell 33. Shoulder 118 (see FIG. 2) rests on top surfaces of track walls 132, 134. Distal end 113 of second portion 116 of cannula block body 110 is sized and configured to fit within track walls 132, 134. Block retentive portions 42 are similarly sized and configured to fit with walls 73, 74 of bottom shell 33. Wall 73 includes a recess 136 which is sized and configured to receive one of block retentive portions 42.

After biopsy device 1 is actuated, compression spring 24 moves cannula block 22 from its retracted position (see FIGS. 3A and 3C) to its extended position (see FIGS. 3B and 3D). During this movement, shoulder 118 rides along the top surfaces of track walls 132, 134. A close fit that is generally without engagement between distal end 113 of second portion 116 and track walls 132, 134 and/or between block retentive portions 42 and walls 73, 74 helps maintain axially straight movement of cannula block 22 when biopsy device 1 is triggered.

Face 112 of cannula block 22 initially contacts stop 120 but does not contact stop 121 due the asymmetry of face 112 relative to stops 120, 121. When cannula block 22 contacts stop 120, cannula block 22 rotates slightly as shown in FIGS. 7C and 7D before cannula block 22 contacts stop 121. This change in the direction of movement of the cannula block 22 from axial motion to a second direction that includes a component transverse to the axial direction can cause friction between stylet 24 and cannula 21, decreasing or preventing recoil of cannula 21 and cannula block 22. Relief portion 130 provides space between wall 73 and cannula block 22 that allows such rotation to occur with one of the block retentive portions 42 being received in recess 136 in wall 73.

In this embodiment, asymmetry in cannula block 22, rather asymmetry in stops 120, 121, causes the described rotation. Thus, cannula block 22 can be used in biopsy devices designed and configured to be used with existing cannula blocks with faces which are symmetric relative to stops 120, 121 while maintaining appropriate alignment between the distal tip of cannula 21 and the distal tip of stylet 55 after biopsy device has been triggered.

Generally, as in the illustrated example, the asymmetry of face 112 will also be relative an axis of biopsy device 1. However, not all asymmetry of face 112 causes the described rotation. For example, the asymmetry between the top of face 112 and the bottom of face 112 does not cause rotation of cannula block 22.

FIGS. 4, 5, and 6A-6D illustrate additional details concerning the structure and operation of biopsy instrument 1. A member 7 is slidably coupled to the housing 2 and is connected to primary bar attachment element 9 of the primary bar 8 via a linkage 38. Overall, member 7 and primary bar 8 are parts of a mechanism that is used to position both stylet 55 and cannula 21 in their retracted positions. Specifically, member 7 and primary bar 8 together move cannula 21 to its retracted position and member 7, primary bar 8, and secondary bar 13 together move stylet 55 to its retracted position. After stylet 55 and cannula 21 are retracted, either side trigger 35 or rear trigger 36 can be used to release the stylet and the cannula to their extended positions.

Figure 5:
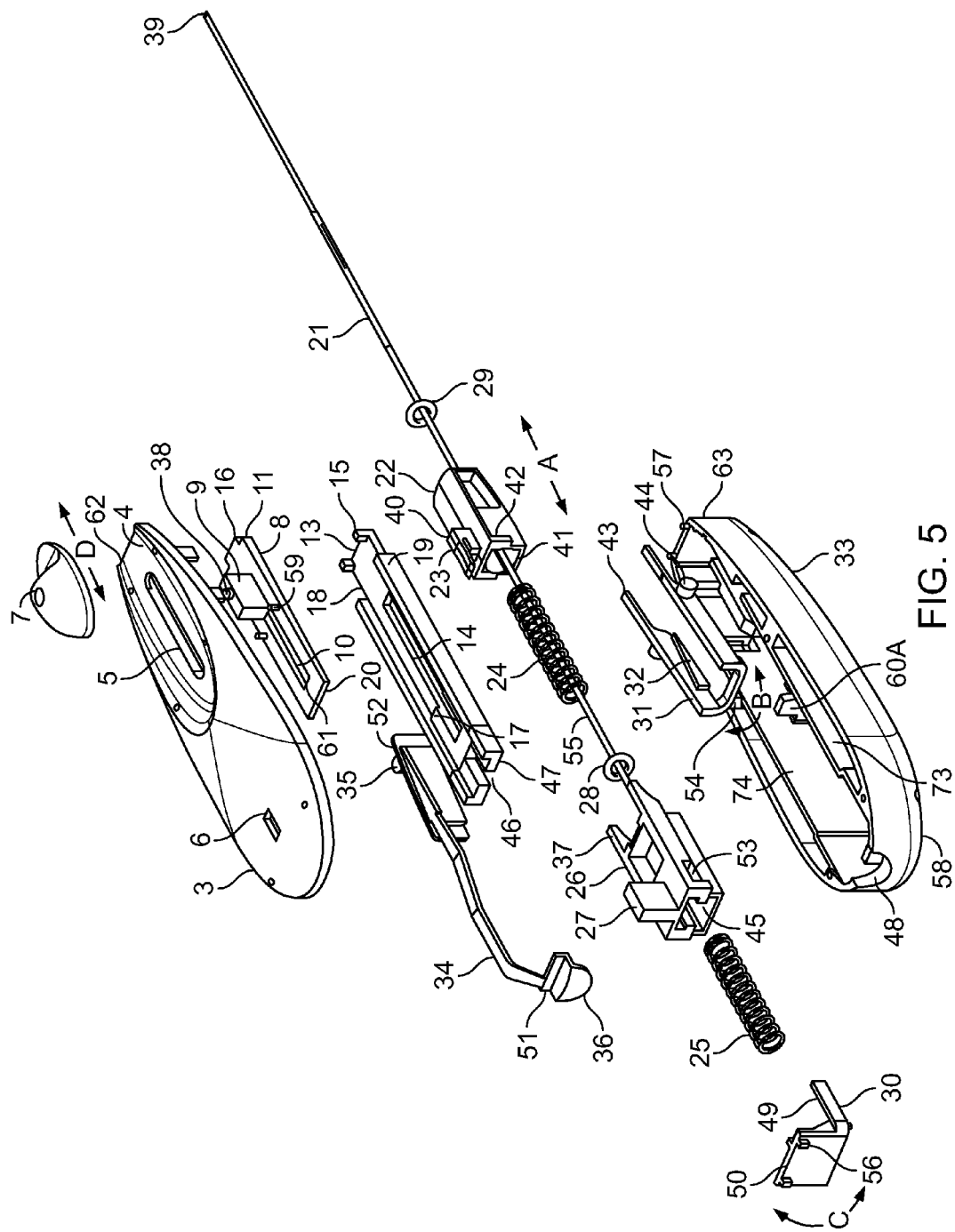
FIG. 5 is an exploded, perspective view of the biopsy instrument of FIG. 4.
Figure 6A:
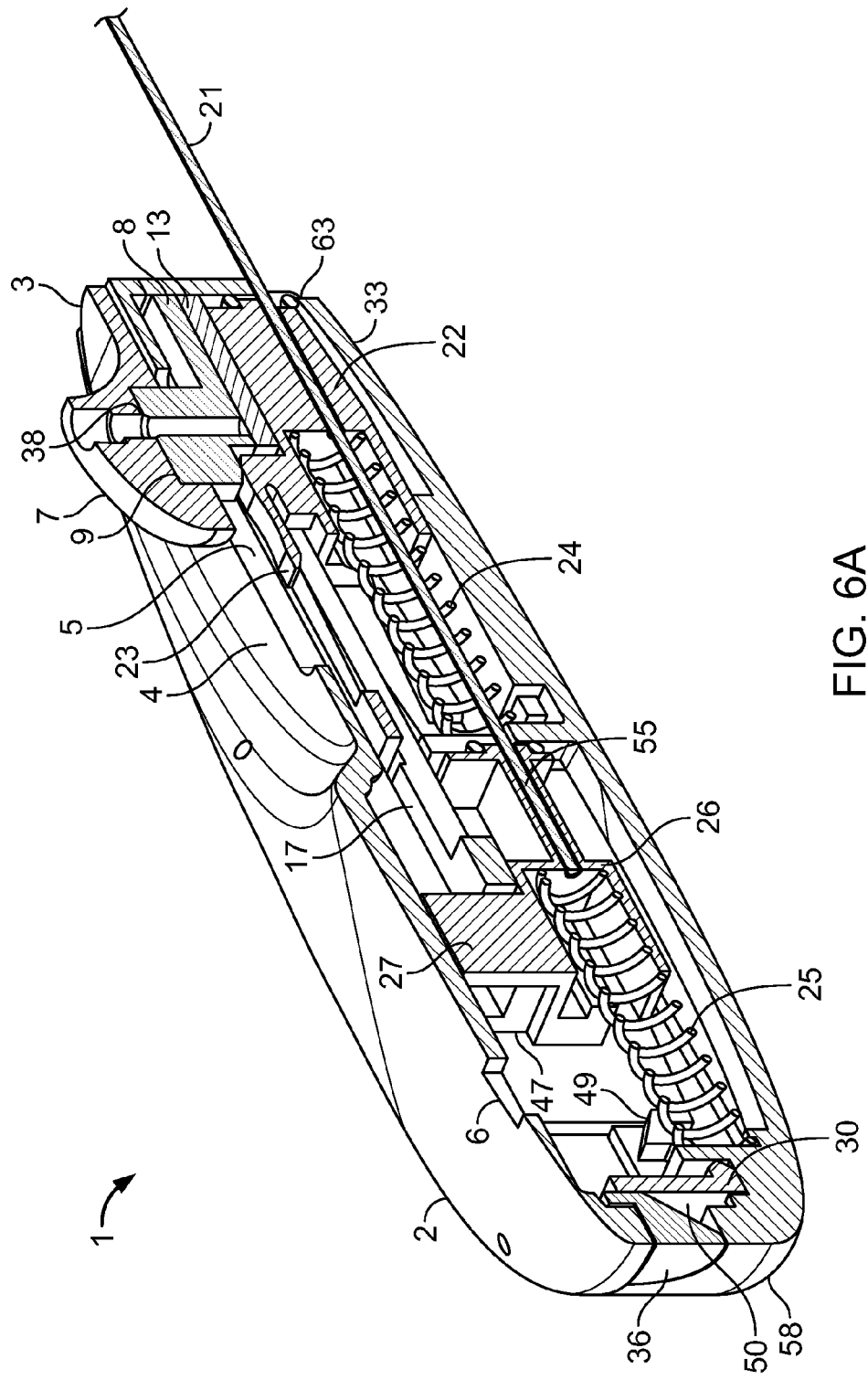
FIGS. 6A-6D illustrate the biopsy instrument of FIG. 4 at various stages of operation.

Referring to FIGS. 5 and 6A, cannula 21 is generally a hollow sheath, e.g., made of stainless steel, that receives stylet 55, which can also be made of stainless steel. At its distal end 39, cannula 21 is configured to sever tissue that has prolapsed into a notch (not shown) formed with at the distal end of stylet 55. Cannula 21 extends into housing 2 wherein the cannula is attached to an axially movable (arrow A) cannula block 22.

Cannula block 22 includes a cannula block hook 23, which extends through primary bar elongate perforation 10 and secondary bar elongate perforation 14 when instrument 1 is assembled. Cannula block hook 23 is engaged at its rear surface 40 by primary bar attachment element 9 during use (described below). Cannula block first raised portion 23 also engages primary bar 8 at its proximal end 20 of primary bar 8 (described below). Cannula block 22 also includes an orifice 41 adapted to receive a first compression spring 24, e.g., a stainless steel spring, e.g., having a spring rate of 9.77 lb/in, and two cannula block retentive portions 42. First compression spring 24 engages cannula block 22 and biases cannula block 22 distally. Cannula block retentive portions 42 are raised portions on either side of cannula block 22, and are adapted to engage cannula block receiver 31 and cannula block receiver locking surfaces 32.

Cannula block receiver 31 can be, e.g., a prong-shaped element having two arms 43 adapted to receive cannula block 22. Cannula block receiver is pivotally attached to bottom shell 33 by linkages 44, which allow cannula block receiver 31 to pivot (arrow B). Cannula block receiver also includes cannula block receiver locking surfaces 32, which are, e.g., raised and angled surfaces adapted to guide cannula block 22 into cannula block receiver 31, and to engage cannula block retentive portions 42.

Stylet 55 is slidably and coaxially located in cannula 21. Stylet 55 has a distal end (not shown) configured to penetrate tissue and a notch (not shown) for collecting a tissue sample. Examples of suitable stylet 55 and cannula 21 configurations are exemplified by the ASAP™ Automated Biopsy System having a Delta Cut® needle or a Channel Cut® needle (available from Boston Scientific Corp., Natick, Mass.), and described in Chu, U.S. Pat. No. 5,989,196, hereby incorporated by reference. From distal end (not shown), stylet 55 extends into housing 2 where stylet 55 is attached to an axially movable stylet block 26.

Stylet block 26 includes two arms 37, which are adapted to contact cannula block receiver 31 around stop block 60A of bottom shell 33 during firing of the instrument (described below). Stylet block 26 also includes a stylet block raised portion 27, which is adapted to be received between the arms 47 of secondary bar 13. Stylet block 26 also includes an orifice 45 adapted to receive a second compression spring 25, e.g., a stainless steel spring having a spring rate of 9.77 lb/in, and two stylet block retentive portions 53, e.g., notches adapted to be received by stylet block receiver 30 and stylet block locking surfaces 49.

Stylet block receiver 30 is pivotally attached to bottom shell 33 by linkages (not shown), which allow stylet block receiver 30 to pivot (arrow C). Stylet block receiver 30 is a generally L-shaped element that includes a rear surface 50 that can contact rear trigger 36 on trigger bar 34. Stylet block receiver 30 also includes stylet block locking surfaces 49, which are, e.g., raised and angled surfaces adapted to guide stylet block 26 into stylet block receiver 30 and to engage stylet block retentive portions 53. Stylet block receiver can also include two raised surfaces 56 on rear surface 50 of stylet block receiver 30, which can be configured to receive rear trigger 36.

Trigger bar 34 is a generally elongate element having a rear trigger 36 at its proximal end 51 and a side trigger 35 near its distal end 52. Rear trigger 36 is, e.g., a portion of trigger bar 34 formed in the shape of tab or button. Rear trigger 36 is adapted to contact rear surface 50 of stylet block receiver 30. Side trigger 35 can also be a portion of trigger bar 34 formed in the shape of tab or button.

Figure 7A:
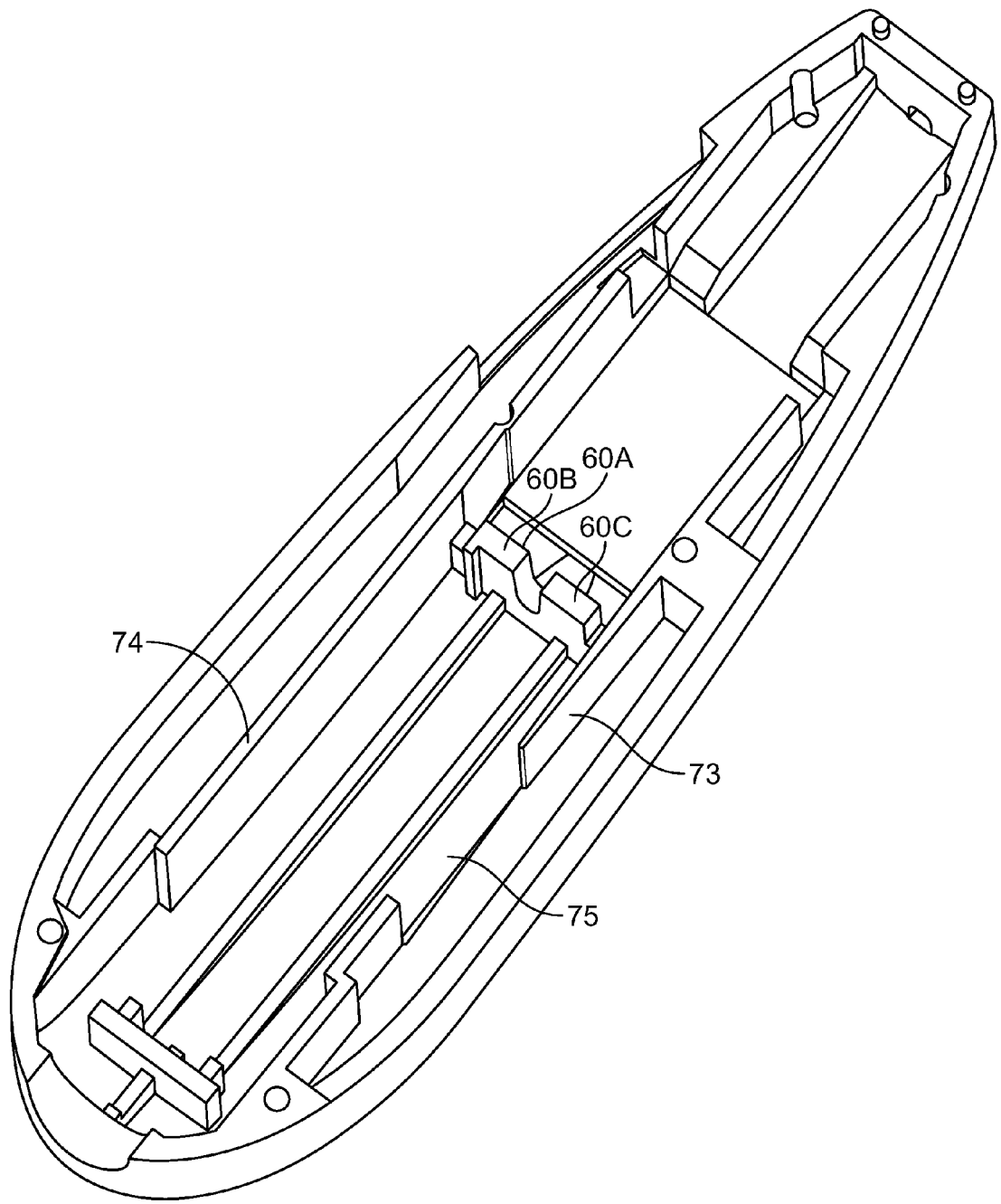
FIGS. 7A-7B is an enlarged view of an embodiment of the present invention.
Figure 7B:
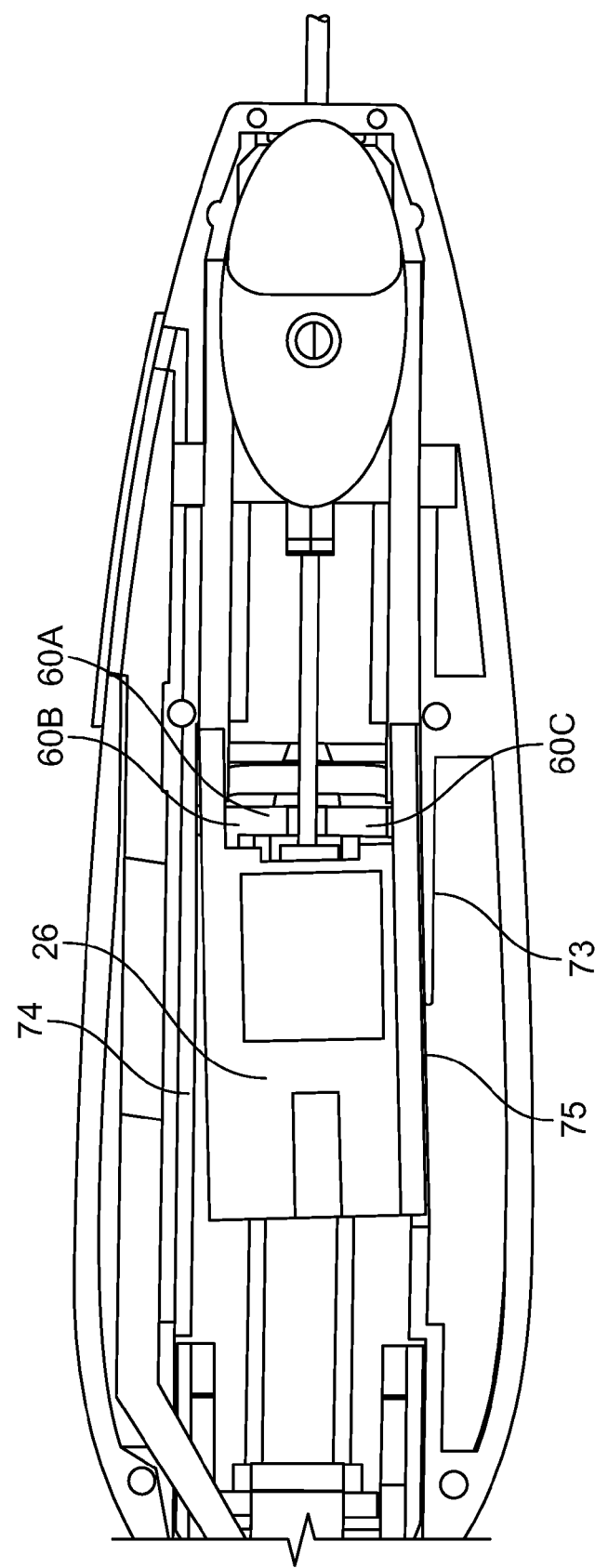

Bottom shell 33 of housing 2 includes stop block 60A, which is situated proximally to cannula block receiver. Bottom shell 33 can also include first 73 and second 74 walls formed therein, between which stylet block 26 and/or cannula block 22 move during operation of instrument 1. FIGS. 7A and 7B illustrate one embodiment of stop block 60A. Referring to FIG. 7A, stop block 60A can be formed such that one side (e.g., 60B) of stop block 60A is slightly thicker, e.g., about $1/8^{th}$ of an inch thicker, than the other side (e.g., 60C), of stop block 60A. In such an embodiment, when stylet block 26 contacts stop block 60A (see FIG. 7B), stylet block 26 rotates slightly to cause friction between stylet 24 and cannula 21, decreasing or preventing recoil of stylet block 26 during firing of the instrument (described below). Accordingly, wall 73 can include a gap 75, which allows stylet block 26 to rotate between first wall 73 and second wall 74 (see FIG. 7B).

Bottom shell 33 includes a first recessed portion 48 or perforation at its proximal end 58 adapted to receive rear trigger 36, and a second recessed portion 54 or perforation adapted to receive side trigger 35. Bottom shell 33 can also include raised portions 57 at distal end 63 of the bottom shell. In some embodiments of the present invention, these raised portions can be used for joining primary bar 8 to bottom shell 33 by at least one (e.g., two) spring(s) (not shown). Specifically, spring(s) (not shown) can be connected to raised portions 57 on bottom shell 33 at one end, with the other end of the spring(s) (not shown) being attached to optional raised portions 59 on primary bar 8. The inclusion of springs connecting primary bar 8 and bottom shell 33 results in the primary bar 8 being biased toward the distal end 62 of top shell 3.

Top shell 3 of housing 2 includes a recessed portion 4 adapted to allow member 7 to slide longitudinally (arrow D) within the recessed portion. Member 7 can take any shape, e.g., a formed button, tab, or finger grip. Top shell 3 also includes elongate perforation 5, through which member 7 and primary bar attachment element 9 are connected by linkage 38. Top shell 3 can also include at least one perforation, e.g., window 6, which can be utilized as an indicator (described below).

Primary bar 8 includes primary bar attachment element 9, which serves, in part, to attach primary bar 8 to member 7 via linkage 38. Primary bar 8 also has a surface 12 that can contact rear surface 40 of cannula block hook 23. Primary bar 8 also includes two recessed portions 11 at its distal end 16, which are adapted to engage secondary bar raised portions 15 during use of the instrument. Primary bar 8 also includes an elongate perforation 10 through which cannula block hook 23 extends.

Secondary bar 13 includes secondary bar raised portions 15, adapted to be received by primary bar recessed portions 11. At proximal end 46, secondary bar 13 includes two arms 47 adapted to engage and receive stylet block raised portion 27 during use of the instrument. Secondary bar also includes also includes an elongate perforation 14 (through which cannula block hook 23 extends), and secondary bar stops 17. Secondary bar also includes guide surfaces 19 adapted to receive and guide primary bar in a slidable manner during use of the instrument.

In some embodiments of the present invention, instrument 1 includes a first 29 and/or a second 28 O-ring, which can act to absorb shock, thus affording more comfort to the user (e.g., by decreasing vibration) and decreasing sound that emanates from the instrument during use.

In some embodiments, window 6 in top shell 3 can act as a visual indicator (or as part of a visual indication system), which signals when stylet 55 is in its retracted position (retracted position). The indication system can include one or more perforations (e.g., window 6 in top shell 4) formed in housing 2 that allow a user to detect a change in the position of stylet block 26. For example, perforation(s) can be formed on housing 2 such that stylet block raised portion 27 covers the window(s) when the stylet block 26 is in its extended position. When stylet block 26 is retracted, stylet block raised portion 27 slides away from window(s) and uncovers interior portions of instrument 1. The interior portions can be colored, e.g., red, for enhanced visibility. In other embodiments, perforation 6 can be aligned with stylet block raised portion 27 which has a first color, e.g., red, and the interior portions can have a second color, e.g., green. When stylet block 52 is moved from its extended position to its retracted position, the color visible through window(s) changes from the second color to the first color to indicate that instrument 1 is retracted. Alternatively or in addition, instrument 1 can include a perforation(s) in housing 2 aligned with cannula block 23 to indicate the position of the cannula block. For example, cannula block 23 can be formed with portions with different colors as described above.

FIGS. 6A-6D illustrate a sequence of the operation of instrument 1. Referring to FIG. 6A, instrument 1 is in its rest position, e.g., as taken out of its packaging. Cannula block 22 and stylet block 26 are at their most distal, extended positions. Member 7 and both primary 8 and secondary 13 bars are in a distal position.

Figure 6B:
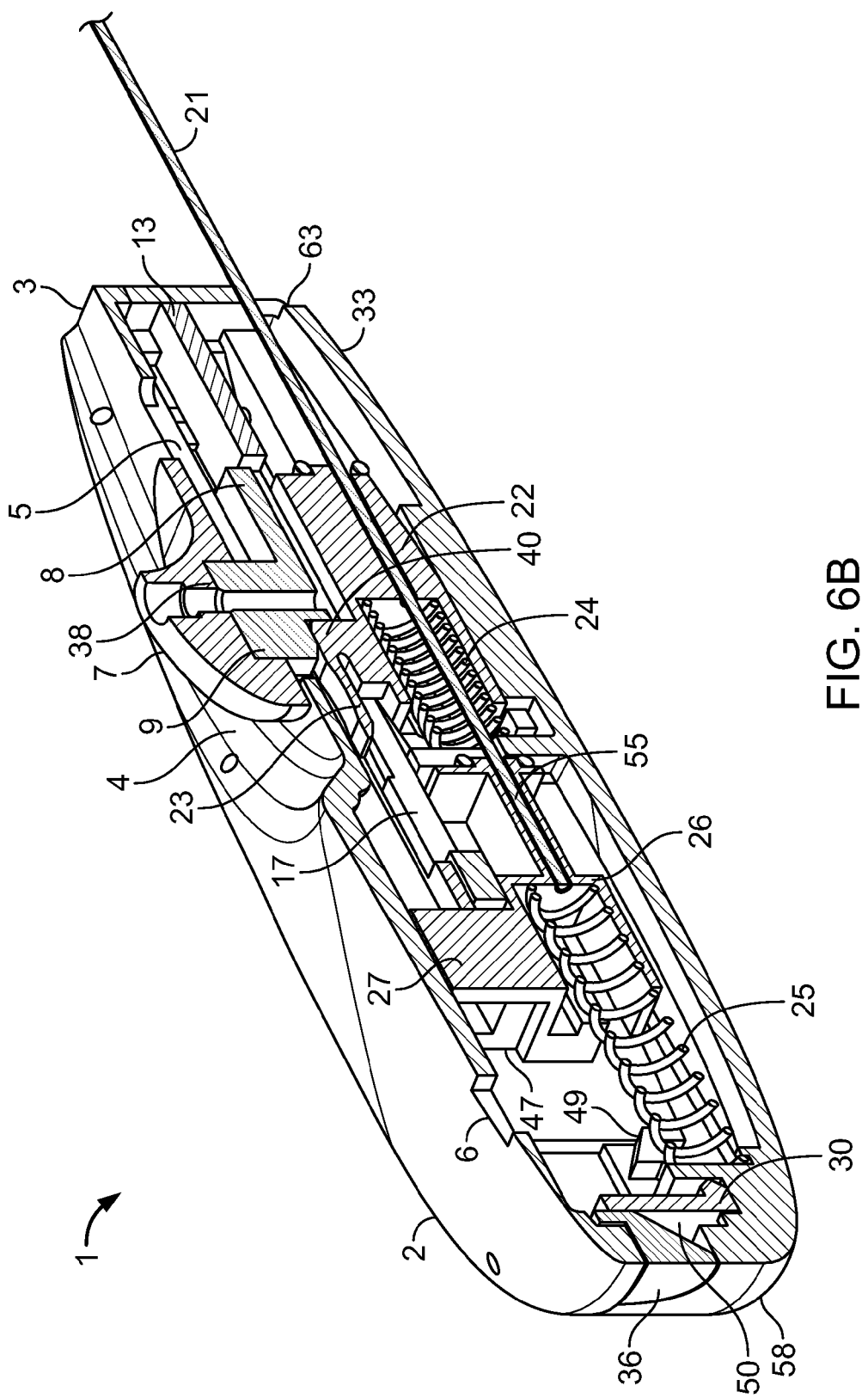

To position cannula block 22 and stylet block 26 in their retracted positions, member 7 is engaged, e.g., moved (retracted) toward the proximal end of instrument 1, two times. Referring to FIG. 6B, when member 7 is engaged the first time, primary bar 8 contacts rear surface 40 of cannula block hook 23, and both primary bar 8 and cannula block 22 are moved in a proximal direction. As a result, cannula block 22 and cannula 21 are pushed proximally until cannula block retentive portions 42 engage cannula block receiver locking surfaces 32. As cannula block receiver 31 receives cannula block 22, cannula block receiver 31 rotates (arrow B) to allow cannula block retentive portions 42 to engage cannula block receiver locking surfaces 32. Cannula block receiver arms 43 press against top shell 3 to bias the rotation of cannula block receiver 31 to a clockwise (arrow B) direction. Once cannula block receiver locking surfaces engage, e.g., lock into, cannula block retentive portions 42, the cannula block 22 and cannula 21 remain in their retracted positions (FIG. 6B). In this position, first compression spring 24 is compressed between cannula block 22 and stop block 60A in bottom shell 33. Member 7 is then released by the user and allowed to return to its distal position, e.g., aided by a spring (not shown).

Figure 6C:
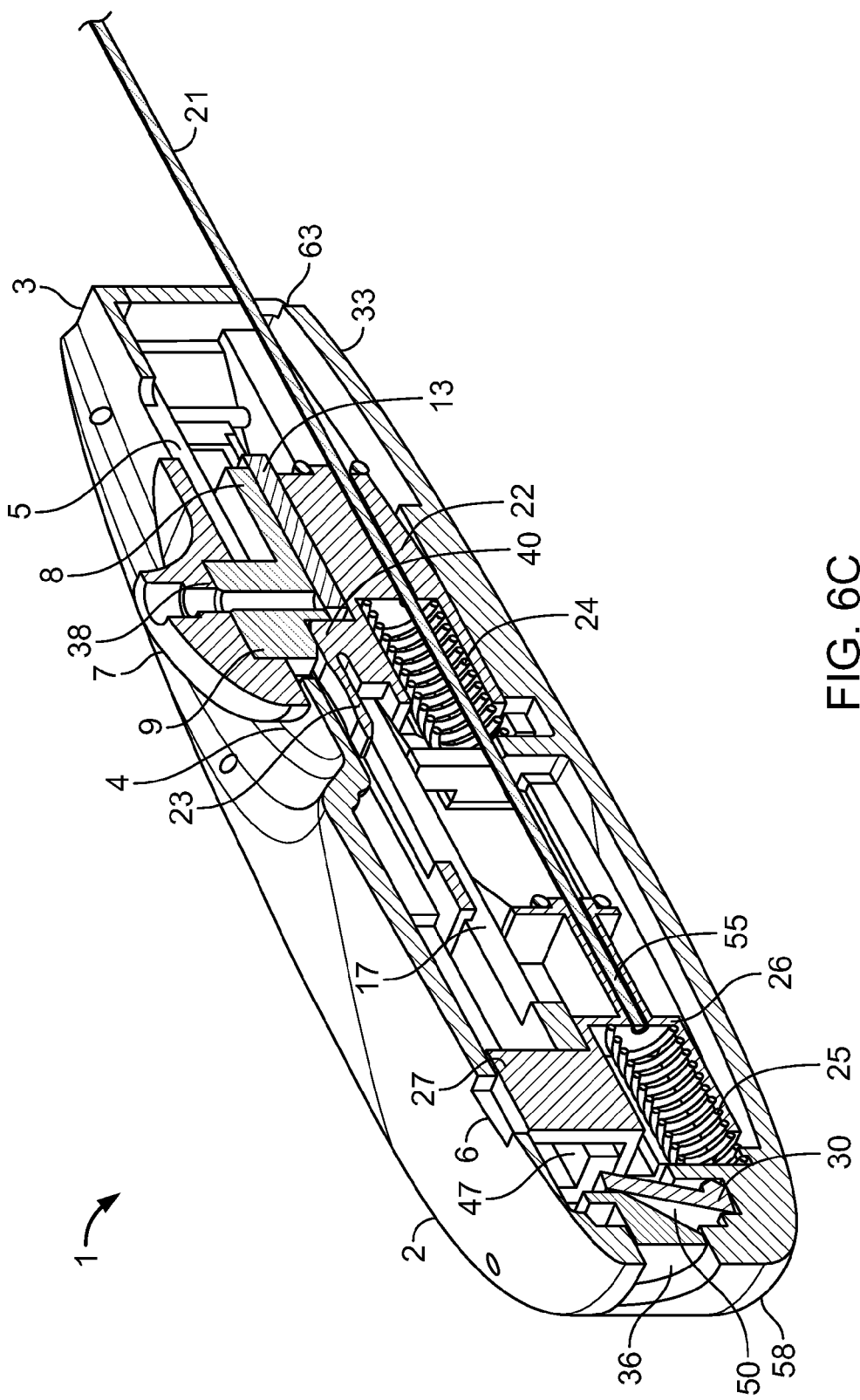
Figure 6D:
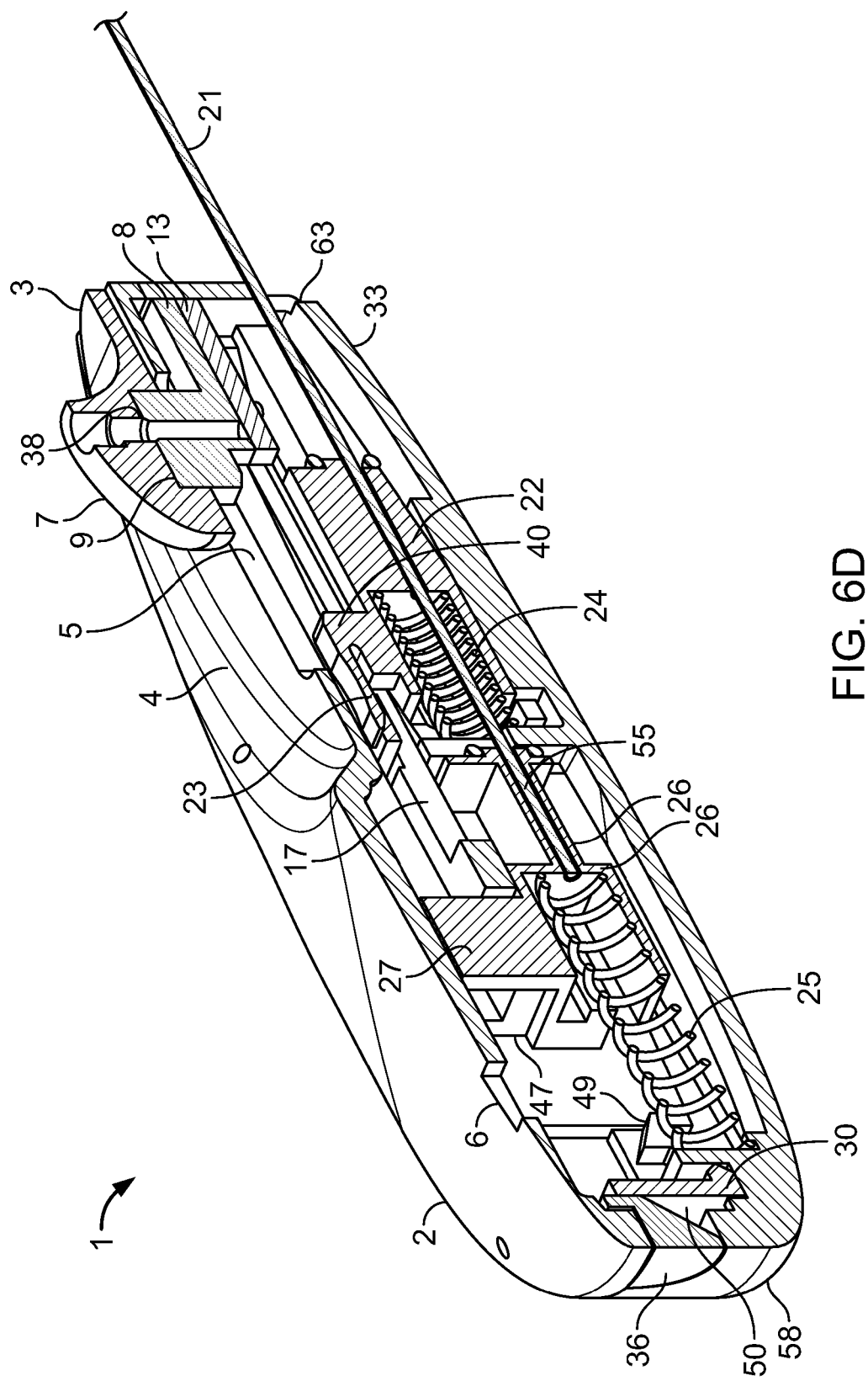

When member 7 is engaged the first time, primary bar 8 is in a first position and not aligned with stops 17 on secondary bar 14. As a result, during the first actuation of member 7, primary bar can slide over stops 17. However, as member 7 and primary bar 8 return to their distal position after the first actuation, cannula block hook 23 engages surface 61 at proximal end 20 of primary bar 8. When cannula block hook 23 engages surface 61, primary bar rotates or flexes slightly to a second position, such that proximal end 20 of primary bar 8 aligns with stops 17 of secondary bar 13. As a result, member 7, primary 8 and secondary 13 bars all move together when member 7 is engaged a second time. Specifically, when member 7 is engaged a second time, primary bar 8 contacts rear surface 40 of cannula block hook 23, proximal end 20 of primary bar 8 contacts secondary bar stops 17, and secondary bar 13 arms engage stylet block raised portion 27. As a result, stylet block 26 and stylet 55 are pushed proximally until stylet block retentive portions 53 engage stylet block receiver 30 and stylet block receiver locking surfaces 49. Once stylet block receiver locking surfaces 49 engage, e.g., lock into, stylet block receiver locking surfaces 49, stylet block 26 and stylet 55 remain in their retracted positions (FIG. 6C). In this position, second compression spring 25 is compressed between stylet block 26 and stylet block receiver 30. Referring to FIG. 6C, both cannula 21 and stylet 55 are fully retracted and prepared for use. Cannula block 22 and stylet block 26 are at their most proximal, retracted positions. Instrument 1 retracted and ready to be triggered or triggered.

To fire instrument 1, distal end of stylet (not shown) is placed adjacent to a target area, and either side trigger 35 or rear trigger 36 is engaged. To engage rear trigger 36, the rear trigger is pushed distally, e.g., using an index finger, which causes rear trigger 36 to push rear surface 50 of stylet block receiver 30. As a result, stylet block receiver 30 pivots (arrow C) to disengage stylet block retentive portions 53 from stylet block receiver locking surfaces 49. Upon disengagement, stylet block 26 and stylet 55 are propelled distally by the spring force of second compression spring 25, which allows stylet 55 to penetrate the targeted area. Stylet block 26 then strikes cannula block receiver 31 (FIG. 6D), causing it to pivot (arrow B) to disengage cannula block retentive portions 42 from cannula block receiver locking surfaces 32. Upon disengagement, cannula block 22 and cannula 21 are propelled distally by the spring force of second compression spring 24, which allows cannula 21 to slide over stylet 55 and to sever a specimen that has prolapsed into notch (not shown) within stylet 55.

Instrument 1 can then be withdrawn. The specimen can be removed from stylet notch (not shown) by engaging member 7 once to retract cannula 21 and expose stylet 55. The specimen can be placed on a slide or in a preservative solution. If desired, member 7 can be engaged to retract and position stylet 55 to collect another specimen.

Side trigger 35 is engaged by pushing the side trigger 35 distally, e.g., using an index finger, which causes trigger bar 34 to move distally as well. Accordingly, rear trigger 36 also moves distally, which causes instrument 1 to fire as described above.

Figure 8A:
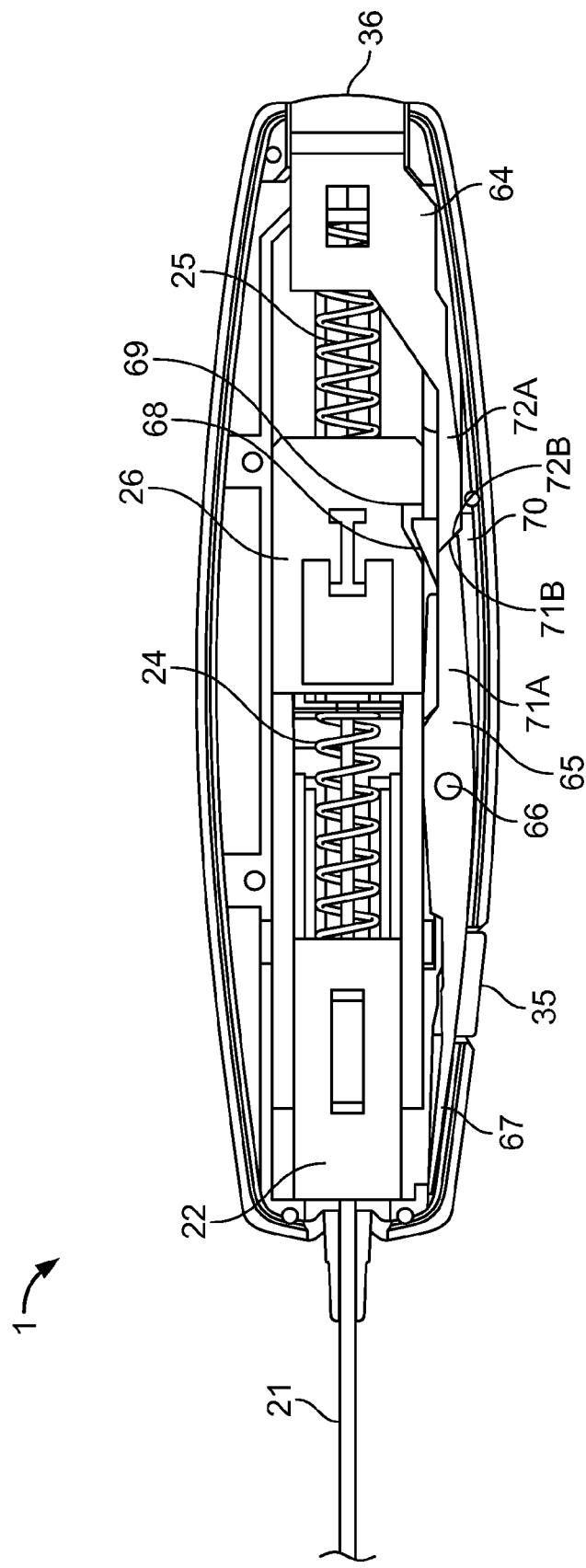
FIGS. 8A-8C illustrate another embodiment of the biopsy instrument at various stages of operation.
Figure 8B:
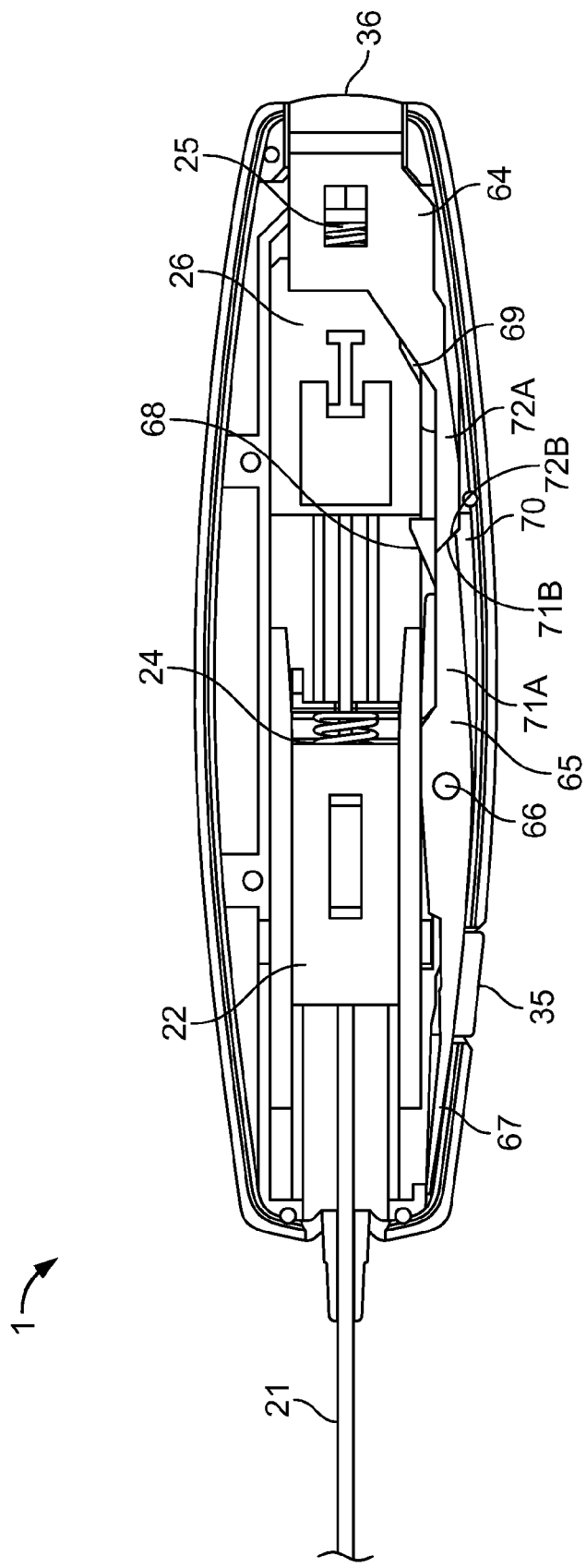
Figure 8C:
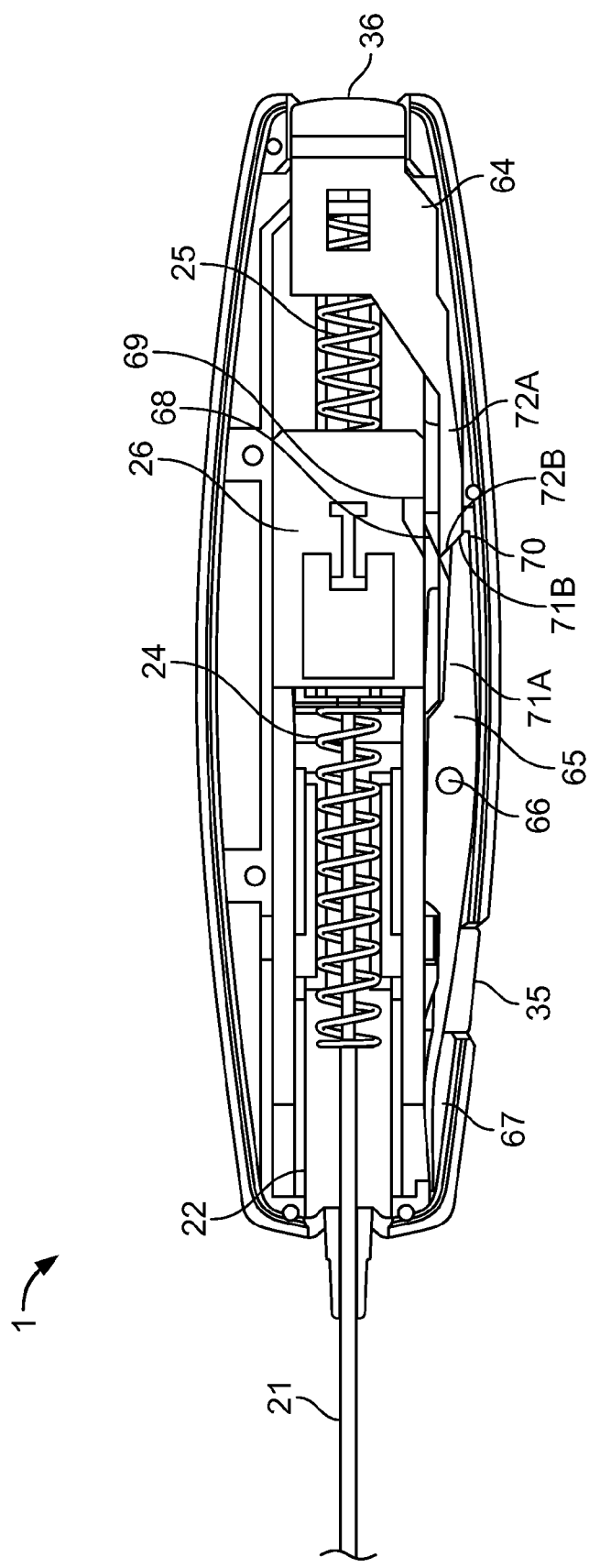

FIGS. 8A-8C illustrate an alternative embodiment of the present invention, wherein biopsy instrument 1 includes an alternative firing mechanism. Referring to FIG. 8A, wherein instrument 1 is in a resting position, trigger bar 34 is replaced with a firing mechanism that includes rear trigger element 64 and side trigger element 65. Rear trigger element 64 includes rear trigger 36 and rear trigger element angled end 72A. Rear trigger element angled end 72A includes an angled surface 72B. Angled surface 72B is adapted to contact another angled surface, angled surface 71B, of side trigger element 65 at junction 70. Side trigger element 65 includes side trigger 35 and side trigger element angled end 71A. Side trigger element angled end 71A includes angled surface 71B. Angled surface 71B is adapted to contact angled surface 72B at junction 70. Side trigger element 65 also includes retentive portion 68, which is adapted to contact and retain stylet block 25 in a retracted position (see FIG. 8B). In this embodiment, stylet block 26 includes stylet block notch 69, which is engaged by retentive portion 68 when biopsy instrument 1 is at rest (e.g., after firing). Retentive portion 68 is located next to angled surface 71B at side trigger element angled end 71A. Side trigger element 65 also includes side trigger element pivot 66 and leaf spring end 67. Side trigger element can be pivotally connected to bottom shell 33.

In this alternative embodiment, the instrument 1 is retracted in a manner similar to that described above, i.e., member 7 is engaged two times. Referring to FIG. 8C (wherein instrument 1 is illustrated in the process of firing), instrument 1 can be triggered using either side trigger 35 or rear trigger 36. To engage rear trigger 36, rear trigger is pushed (leftward in FIG. 8C), e.g., using an index finger, which causes rear trigger element 64 to move in the same direction (leftward in FIG. 8C). This motion causes angled surface 72B to slide against angled surface 71B at junction 70, causing side trigger element 65 and retentive portion 68 to rotate about pivot 66, disengaging retentive portion 68 from stylet block 26. Stylet 55 and cannula 21 are then discharged and propelled forward as described above.

To fire the instrument using side trigger 35, the side trigger is pushed (upward in FIG. 8C) e.g., using an index finger, which causes side trigger element angled end 71B and retentive portion 68 to rotate about pivot 66, disengaging retentive portion 68 from stylet block 26. The instrument then discharges as described above. Leaf spring end 67 biases retentive element 68 to a resting position (see FIGS. 8A and 8B).

In some embodiments, housing 2 and/or member 7 can each be made of different materials, e.g., to enhance the grip or "feel" of instrument 1. For example, housing 2 and/or member 7 can be formed of materials with different hardness, e.g., a core of relatively hard material and an outer layer of relatively soft material. The outer layer can be a foamy material, such as a urethane, to enhance the grip and/or to absorb vibrations from the firing of instrument 1. Each of housing 2 and/or member 7 can be formed with two or more different materials.

The components of instrument 1 described above can be formed by conventional injection molding techniques, e.g., of polycarbonate and/or ABS. Stylet 55, cannula 21, first 24 and second 25 compression springs can be formed of stainless steel.

The term "patient" includes all animals, human or non-human. Examples include birds, reptiles, amphibians, and mammals, e.g., humans, other primates, pigs, rodents such as mice and rats, rabbits, guinea pigs, hamsters, cows, horses, cats, dogs, sheep and goats. Preferred patients are humans, farm animals, and domestic pets such as cats and dogs.

The biopsy instrument can be used for sampling in any part of a body, e.g., stomach, colon, rectum, mouth/pharynx, esophagus, larynx, liver, pancreas, lung, breast, cervix uteri, corpus uteri, ovary, prostate, testis, bladder, skin, kidney, brain/central nervous system, head, neck and throat, among others.

A number of embodiments of the invention have been described. Nevertheless, it will be understood that various modifications may be made without departing from the spirit and scope of the invention. Accordingly, other embodiments are within the scope of the following claims.

What is claimed is:

1. A device, comprising:
   a housing including a stop with a first contact portion and a second contact portion;
   a cannula having a portion in the housing; and
   a movable cannula block in the housing, the moveable cannula block attached to the cannula, the movable cannula block having a distal end with a face that includes a first portion and a second portion recessed relative to the first portion of the face, the recessed second portion disposed in alignment with the second contact portion of the stop such that movement of the cannula block towards the stop brings the first portion of the face of the cannula block into contact with the first contact portion of the stop and rotates the cannula block to bring the recessed second portion into contact with the second contact portion of the stop;
   wherein the housing includes ribs defining a channel that receives at least part of the cannula block, the channel having a channel width; and
   wherein the cannula block has a middle portion disposed proximally of the asymmetric distal end of the cannula block and a distal end width of the part of the cannula block received in the channel is greater than a width of the part of the cannula block received in the channel at the middle portion and less than the channel width;
   wherein the width of part of the cannula block received in the channel is a distance along a line perpendicular to the ribs defining the channel from an outermost surface on a first side of the part of the cannula block received in the channel to an outermost surface on a second side, opposite the first side, of the part of the cannula block received in the channel.

2. The device of claim 1, wherein the recessed second portion is located at one edge of the face.

3. The device of claim 1, wherein the housing comprises a wall with a gap sized to accommodate a portion of the cannula block.

4. The device of claim 3, wherein the wall with the gap is a side wall of a track in which the cannula block is disposed.

5. The device of claim 1, wherein the stop is disposed at a distal end of the housing.

6. The device of claim 1, further comprising a stylet disposed coaxially with the cannula, the stylet at least partially within the cannula.

7. A device, comprising:
   a housing including a stop;
   a longitudinally extending first member having a first portion in the housing and a second portion extending out of the housing; and
   a movable second member in the housing, the second member being connected to the first member, the second member having a distal end with a face that is asymmetric with respect to the stop, the movable second member configured to change movement of the second member from a first direction to a second direction that includes a component transverse to the first direction upon contact with the stop;
   wherein the face of the second member includes a recessed portion disposed in alignment with a contact portion of the stop;
   wherein the housing includes ribs defining a channel that receives at least part of the second member, the channel having a channel width; and
   wherein the second member has a middle portion disposed proximally of the asymmetric distal end of the second member and a distal end width of the part of the second member received in the channel is greater than a width of the part of the second member received in the channel at the middle portion and less than the channel width;
   wherein the width of part of the second member received in the channel is a distance along a line perpendicular to the ribs defining the channel from an outermost surface on a first side of the part of the second member received in the channel to an outermost surface on a second side, opposite the first side, of the part of the second member received in the channel.

8. The device of claim 7, wherein the recessed portion is located at one edge of the face.

9. The device of claim 7, wherein the housing comprises a wall with a gap sized to accommodate a portion of the movable second member.

10. The device of claim 9, wherein the wall with the gap is a side wall of a track in which the second member is disposed.

* * * * *